United States Patent [19]

Bolhofer

[11] 4,144,338
[45] Mar. 13, 1979

[54] N-PYRIMIDINYL-N-DIALKYLAMINOALKYL UREAS

[75] Inventor: William A. Bolhofer, Frederick, Pa.

[73] Assignee: Merck & Co., Inc., Rahway, N.J.

[21] Appl. No.: 769,475

[22] Filed: Feb. 17, 1977

[51] Int. Cl.$^2$ .................. A61K 31/505; C07D 239/42
[52] U.S. Cl. .................................... 424/251; 424/249; 424/250; 544/182; 544/224; 544/320; 544/321; 544/323; 544/329; 544/330; 544/332; 544/336; 544/409
[58] Field of Search ............... 260/256.4 N; 544/329, 544/332; 424/251

[56] References Cited

U.S. PATENT DOCUMENTS

| | | | |
|---|---|---|---|
| 3,705,159 | 12/1972 | Schneider et al. | 260/256.4 N |
| 3,759,921 | 9/1973 | Paget | 260/256.4 N |
| 3,950,537 | 4/1976 | DeBenneville et al. | 424/322 |
| 4,008,235 | 2/1977 | Lesher et al. | 424/251 |

FOREIGN PATENT DOCUMENTS 1444558  8/1976  United Kingdom.

*Primary Examiner*—Coughlan, Jr. Paul M.
*Attorney, Agent, or Firm*—David L. Rose; J. Jerome Behan

[57] ABSTRACT

Organic chemical compounds based upon the urea molecule are disclosed which have potent gastric secretion inhibitory properties. The urea is substituted with a 6 membered heterocyclic substituent containing 2 or 3 heteroatoms, and also with a substituted amino alkyl group. Further substitution is also possible. The compounds have profound effects on the inhibition of gastric secretions in the gastro-intestinal tract, and compositions for such uses are also disclosed.

9 Claims, No Drawings

N-PYRIMIDINYL-N-DIALKYLAMINOALKYL UREAS

BACKGROUND OF THE INVENTION

Excess secretion of gastric acid can cause indigestion and stomach distress and, if prolonged, can result in ulcer formation. Treatment of excess secretion of gastric acid has heretofore consisted mainly of a bland diet, abstinence from certain foods and the use of antacids to neutralize the gastric acid after it is secreted into the stomach. An improved method of treatment would result from the inhibition of gastric acid secretion. It is thus an object of the present invention to provide compounds which inhibit gastric acid secretion. Another object is to provide methods for the preparation of these compounds. A further object is to provide pharmaceutical formulations for the administration of these compounds. Still another object is to provide a method to inhibit gastric secretion. These and other objects of the present invention will become apparent from the following description.

DESCRIPTION OF THE INVENTION

The compounds of the instant invention are best described by reference to the following structural formula:

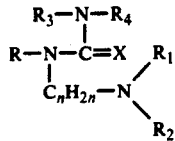

wherein R is a 6 membered heterocyclic ring system containing 2 or 3 nitrogen heteroatoms, which heterocyclic ring may be optionally substituted with from 1 to 3 of loweralkyl, halo, hydroxy, amino, mono or di-loweralkylamino, loweralkoxy or phenylloweralkoxy;

$R_1$ and $R_2$ are independently loweralkyl;

$R_3$ and $R_4$ are independently hydrogen or loweralkyl;

X is oxygen or sulfur; and n is an integer of from 2 to 6, such that the direct linkage between the nitrogen atoms is either two or three carbon atoms.

In the foregoing structural formula R is a heterocyclic moiety consisting of 6 membered heterocycles containing 2 nitrogen atoms such as pyrimidine, pyridazine and pyrazine; and 6 membered heterocycles containing 3 nitrogen atoms referred to as triazines. The heterocyclic group may be optionally substituted with from 1 to 3 of loweralkyl, halo, hydroxy, amino or mono or di-loweralkylamino, loweralkoxy or phenylloweralkoxy.

In the instant specification the term "loweralkyl" is intended to include those alkyl groups of either straight or branched configuration which contain from 1 to 5 carbon atoms. Exemplary of such alkyl groups are methyl, ethyl, propyl, isopropyl, butyl, tertiary butyl, pentyl and the like.

The term "halo" or "halogen" is intended to include the halogen atoms fluorine, chlorine, bromine and iodine.

PREFERRED EMBODIMENTS OF THE INVENTION

The preferred embodiments of the instant invention are realized in the foregoing structural formula wherein:

R is pyrimidinyl, pyridazinyl or pyrazinyl optionally substituted with one to three of methyl, chloro or dimethylamino;

$R_1$, $R_2$, $R_3$ and $R_4$ are independently methyl, ethyl or isopropyl;

n is 2; and

X is oxygen.

Further preferred embodiments are realized when the substituents on the pyrimidinyl group consist of 1 or 2 methyl groups or a chloro and 2 methyl groups. $R_1$ and $R_2$ are isopropyl; and $R_3$ and $R_4$ are methyl.

The compounds of the present invention are prepared by reacting an appropriately substituted alkylene diamine (II) with an appropriately substituted carbamoyl halide or thiocarbamoylhalide (II-A) as described in the following reaction scheme:

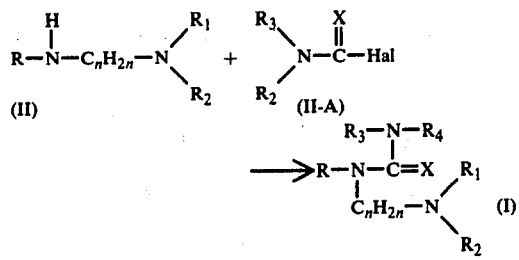

wherein X, n, R, $R_1$, $R_2$, $R_3$ and $R_4$ are as previously defined, and Hal is a halogen. The reaction is generally carried out in an inert solvent, preferably an aromatic solvent such as benzene at a temperature of from about 20° to 120° C., preferably from about 75° to 100° C. Where the reaction temperature exceeds the boiling point of the reaction solution, the reaction is carried out under pressure. It is preferred to contain in the reaction mixture a scavenger for the hydrohalic acid liberated during the course of the reaction. Non-reactive bases, either inorganic or organic may be employed such as triethylamine, pyridine, sodium carbonate, and the like. The base is required in a single molar equivalent to the acid being liberated, however, excess base has not been found to be detrimental. The product (I) is isolated and purified as the free base or acid addition salt using known techniques. The halogen Hal may be any halogen, however, it is preferred to use chlorine.

Optionally the diamine (II) may be converted into an anion before it is reacted with the carbamoylhalide. Reactive alkali metal compounds such as sodium hydride, lithium aluminum hydride, butyl lithium and the like may be employed. The diamine and the alkali metal compound are combined preferably at room temperature in the foregoing inert solvent in equivalent amounts. If this method is employed the acid scavenger is not needed since an alkali metal halide is the reaction by-product.

The alkylene diamine starting materials (II) for the foregoing processes are made from the appropriately substituted heterocyclic amine wherein the amine function has been activated by a labile activating group. The process is best exemplified by the following reaction scheme:

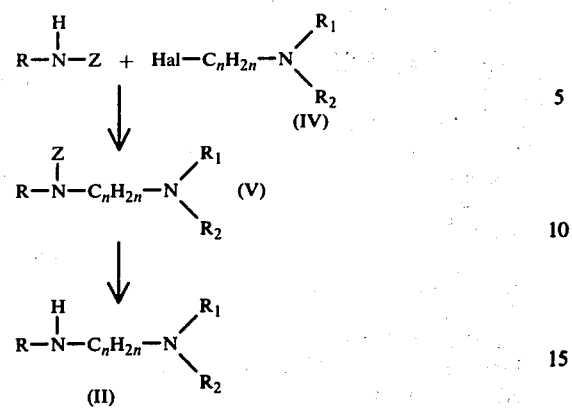

In the foregoing reaction scheme Hal, R, $R_1$, $R_2$ and n are as previously defined and Z is an activating group. The reaction is carried out in the presence of a strong base such as sodium hydride, butyl lithium, lithium diisopropylamide and the like, in an appropriate, nonreactive solvent such as dimethylformamide, toluene, dioxane, and the like. The reaction temperature may be in the range of $-70°$ to about $160°$ C. It is preferred, however, that the reaction temperature be maintained at from about $0°$ to $100°$ C.

The labile activating group (Z) may be an acyl group readily bonded to the amino group and which may be selectively removed therefrom. Examples of such groups are acetyl, formyl, and the like.

The labile activating group is removed hydrolytically with acidic (such as aqueous mineral acid) or basic (such as alkali hydroxide) reagents, under conditions known to those skilled in this art.

Alternatively the substituted ethylene diamines (II) are prepared from appropriately substituted halo heterocyclic compounds (VI). The halogen substituent is displaced by the unsubstituted amino group of an appropriately substituted alkylene diamine (VII) as shown in the following reaction scheme:

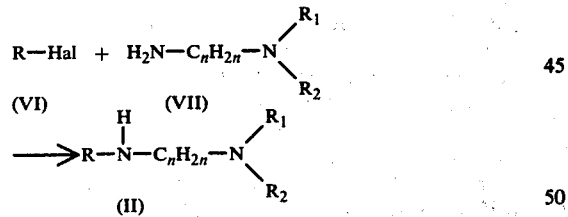

R, $R_1$, $R_2$, Hal and n are as previously defined.

The reaction is carried out generally in the absence of a solvent at temperatures of from about $50°$ to $150°$ C. at from 2 hours to as much as one week for difficult reactions. If a solvent is employed it must have a sufficiently high boiling point to allow the reaction to progress. Dimethylformamide, toluene and xylene are exemplary. Generally the reactions are complete in from about 10 hours to 3 days. For those reactions requiring a prolonged heating period, a catalyst, cuprous chloride, may be employed. The use of catalytic amounts of such catalyst will generally reduce the reaction time to within the preferred range. The products are isolated using techniques known to those skilled in this art.

In addition, the substituted alkylene diamines (II) are prepared from an appropriately alkoxy or alkythio substituted heterocyclic compound (VIII) and the above substituted ethylene diamine (VII) as in the following reaction scheme:

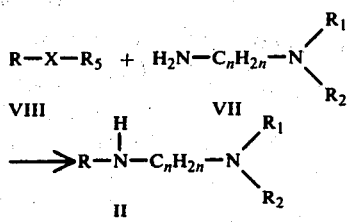

X, R, $R_1$, $R_2$ and n are as previously defined and $R_5$ is loweralkyl, preferably methyl. The reaction is carried out under the conditions described in the immediately preceding paragraph, and the product is isolated using known techniques.

The compounds of the present invention where X is oxygen (I-A) are prepared by reacting a substituted urea (IX) with the above substituted amino alkyl halide (IV) as follows:

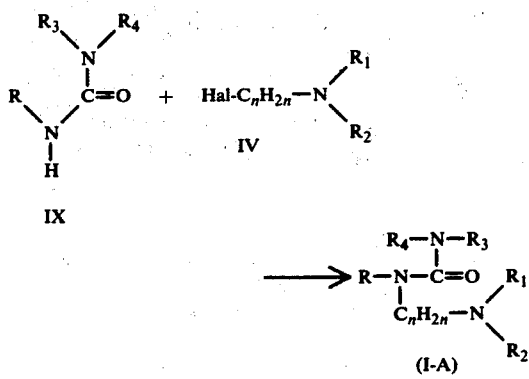

where R, $R_1$, $R_2$, $R_3$, $R_4$, Hal and n are as previously defined. The reaction is carried out by first preparing the alkyl metal, preferably lithium salt of the urea (IX) by treating it with lithium hydride in dioxene or butyl lithium in benzene. The reaction is refluxed for from 1 to 16 hours and then cooled and the substituted amino ethylhalide (IV) added and the reaction refluxed for from 2 to 24 hours. The product is isolated during known means.

The substituted urea compounds (IX) are prepared by reacting an appropriately substituted heterocyclic amine (X) with the above substituted carbamoyl halide (II-A) wherein X is oxygen according to the following reaction scheme:

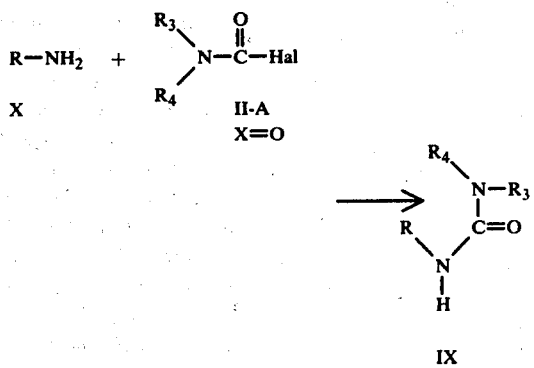

wherein R, R₃, R₄, and Hal are as previously defined.

The foregoing reaction is carried out by combining the heterocyclic amine (X) with two moles of an alkali metal hydride such as sodium hydride or lithium hydride in a solvent and refluxing for from 10 minutes to 4 hours. The carbamoyl halide reagent is added and the reaction mixture then maintained at from room temperature to reflux for from ½ to 6 hours. Preferred solvents are inert solvents such as benzene, toluene, xylene and the like. It is also preferred to have an acid scavenger such as triethyl amine or pyridine to neutralize the liberated hydrohalic acid.

Further, the compounds of the instant invention (I) wherein one of R₃ or R₄ is hydrogen may be prepared by reacting the above alkylene diamine (II) with an appropriately substituted loweralkyl isocyanate or isothiocyanate as follows:

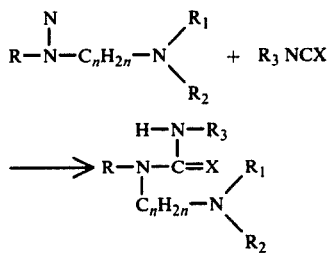

wherein R, R₁, R₂, X and n are as previously defined and R₃ is loweralkyl. The reaction is generally carried out at from 0° C. to the boiling point of the isocyanate or isothiocyanate reagent. Preferably the reaction is stirred at room temperature in an aprotic solvent such as benzene, toluene, xylene, tetrahydrofuran and the like, for from 10 hours to one week. Generally the reaction is complete in from 24 to 72 hours.

The compounds of the present invention where X is oxygen and R₃ and R₄ are hydrogen may be prepared by reacting cyanogen bromide with the above alkylene diamine (II):

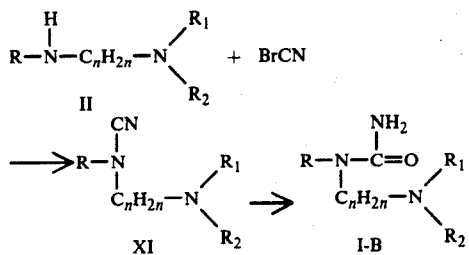

The reaction is generally carried out in a solvent such as tetrahydrofuran with an acid scavenger such as triethyl amine at from 0° to 50° C. for from 6 hours to 3 days. The intermediate cyanamide (XI) is then hydrolized using acid hydrolysis such as aqueous hydrohalic acids at about room temperature for from 5 minutes to 6 hours. Preferably hydrochloric acid is employed at from 4 to 8 normal strength. The product (I-B) is recovered using known techniques.

In addition, the compounds of the present invention wherein X is oxygen (I-A) may be prepared from an appropriately substituted urethane (XII) and ammonia or a substituted amine as follows:

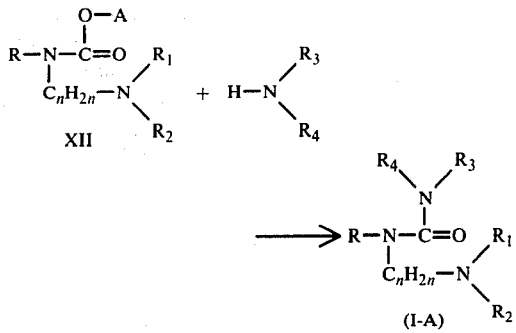

wherein R, R₁, R₂, R₃, R₄, and n are as previously defined and A is a lower alkyl group, a phenyl group or a phenyl group substituted with a non-reactive substituent such as loweralkyl. The unsubstituted phenyl group is preferred. The reaction is optionally carried out in a solvent such as tetrahydrofuran, at from room temperature to the reflux temperature of the reaction mixture. When ammonia is employed, concentrated aqueous ammonia is employed and the solvent may be omitted. In such cases room temperature is adequate to complete the reaction. With substituted amines higher temperatures are beneficial, and occasionally temperatures higher than reflux, in a bomb, are also beneficial. Temperatures to 150° C. may be employed. The reaction is generally complete in from 1 to 24 hours, and the product (I-A) recovered using standard techniques.

The starting urethanes (VII) of the foregoing reaction are prepared from the alkylene diamine (II) and a chloroformate ester (XIII) as follows:

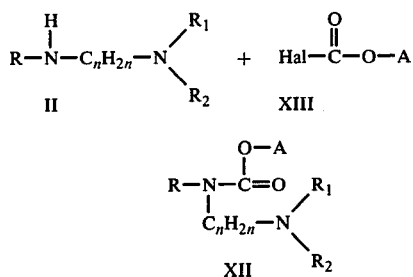

wherein R, R₁, R₂, R₃, R₄, Hal, n, and A are as previously defined. The reaction is carried out in an inert solvent such as tetrahydrofuran, benzene, toluene, xylene, and the like at from 0° to 75° C., preferably room temperature for from ½ to 3 days. An acid scavenger such as triethyl amine or pyridine may also be employed, but its use is not required.

The compounds of this invention may be isolated and used as the free base or as a pharmaceutically acceptable acid addition salt. Such salts are formed by reaction of the free base with the desired inorganic or organic acid. The salts are prepared using methods known to those skilled in this art. Exemplary inorganic acids are hydrohalic acids such as hydrochloric or hydrobromic, or other mineral acids such as sulfuric, nitric, phosphoric and the like. Suitable organic acids are maleic, fumaric, tartaric, citric, acetic, benzoic, succinic, isethionic and the like.

The compounds of the present invention in the described dosages may be administered orally, however, other routes such as intra peritoneal, subcutaneous, intramuscular or intravenous may be employed.

The active compounds of the present invention are orally administered, for example, with an inert diluent or with an assimilable edible carrier, or they may be enclosed in hard or soft gelatin capsules, or they may be compressed into tablets, or they may be incorporated directly with the food of the diet. For oral therapeutic administration, the active compounds of this invention may be incorporated with excipients and used in the form of tablets, troches, capsules, elixirs, suppositories, suspensions, syrups, wafers, chewing gum, and the like. The amount of active compound in such therapeutically useful compositions or preparations is such that a suitable dosage will be obtained. The tablets, troches, pills, capsules and the like may also contain the following: a binder such as gum tragacanth, acacia, corn starch or gelatin; an excipient such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen, or cherry flavoring. When the dosage unit form is a capsule, it may contain in addition to materials of the above type, a liquid carrier such as a fatty oil. Various other materials may be present as coatings or to otherwise modify the physical form of the dosage unit, for instance, tablets, pills or capsules may be coated with shellac, sugar or both. A syrup or elixir may contain the active compounds, sucrose as a sweetening agent, methyl and propyl parabens as preservatives, a dye and a flavoring such as cherry or orange flavor. Of course, any material used in preparing any dosage unit form should be pharmaceutically pure and substantially non-toxic in the amounts employed.

EXAMPLE 1

N,N-Dimethyl-N'-(2-diisopropylaminoethyl)-N'-(4,6-dimethyl-2-pyrimidinyl)urea

A. 2-(2-Diisopropylaminoethylamino)-4,6-dimethyl pyrimidine.

To 600 ml of dry dimethylformamide is added 2-acetamido-4,6-dimethylpyrimidine (34.8 g., 0.21 mole) and 2-diisopropylaminoethyl chloride hydrochloride (48 g., 0.24 mole). The mixture is stirred under nitrogen and sodium hydride (50% in mineral oil) (24.7 g., 0.515 mole) is added in portions over one hour while the temperature is maintained below 45° C. The mixture is then heated at 75°-78° C. for ½ hour and then at 90°-95° C. for 3½ hours. On cooling, ethanol, 25 ml, is added and the solvents removed under reduced pressure. The residue is suspended in 75 ml of 1-propanol and 400 ml of 5N sodium hydroxide and refluxed with stirring for 18 hours. On cooling the mixture is extracted with methylene chloride. The organic extracts are then extracted with dilute hydrochloric acid. The acid extracts are extracted with hexane and then made alkaline with a molar excess of sodium hydroxide. The crude product is extracted from the basic solution with diethyl ether. The ethereal extracts are washed with saturated sodium chloride solution, dried over sodium sulfate and concentrated under vacuum. The residue is distilled and the product diamine (37.2 g., 0.149 mole) collected at 130°-134° C./0.4 mm; melting point 79.5°-82° C.

B. N,N-Dimethyl-N'-(2-diisopropylaminoethyl)-N'-(4,6-dimethyl-2-pyrimidinylurea A mixture of 2-(2-diisopropylaminoethylamino)-4,6-dimethyl pyrimidine (17.0 g. 0.068 mole) and sodium hydride (50% in mineral oil) (4.19 g., 0.86 mole) in 175 ml. of dry toluene is stirred under nitrogen at 85°-95° C. for one half hour and then heated under reflux for one half hour. Dimethylcarbamoyl chloride (8.6 g., 0.08 mole) is added and heating under reflux is continued for twenty-four hours. The reaction is cooled and ethanol (10 ml) and sodium hydroxide (75 ml., 3.3N) are added. The aqueous layer is extracted with methylene chloride and the extracts are dried over sodium sulfate and concentrated to an oil. The oil is distilled at 0.5 mm of Hg and the product boiling at 155°-158° C. is collected.

EXAMPLE 2

N,N-Dimethyl-N'-(2-dimethylaminoethyl)-N'-(2-pyrazinyl)urea Dihydrobromide

To a solution of 2-(2-dimethylaminoethylamino) pyrazine (10 g., 0.0601 mole) and triethylamine (7.2 g., 0.072 mole) in 150 ml of dry benzene is added dimethylcarbamoyl chloride (6.93 g., 0.0645 mole) with stirring. The mixture is refluxed for 18 hours, cooled to room temperature, diluted with 100 ml of ether and filtered. The filtrate is concentrated under vacuum and the residual oil diluted with 250 ml of petroleum ether, treated with charcoal and filtered. Removal of the solvent under reduced pressure gives 13 g. (0.055 mole) of an amber oil. The oil is dissolved in 250 m. of ether and gaseous hydrogen bromide is passed into the solution, the precipitated salt is filtered, redissolved in isopropanol and the solution concentrated to dryness under reduced pressure. The solid is triturated with 35 ml of isopropanol, filtered and recrystallized from ethanol to obtain 12.6 g. (0.031 mole) of N,N-Dimethyl-N'-(2-dimethylaminoethyl)-N'-(2-pyrazinyl)urea dihydrobromide, melting point 157.5°-159.5° C.

EXAMPLE 3

N,N-Dimethyl-N'-(2-dimethylaminoethyl)-N'-(5,6-dimethyl-2-pyrazinyl)urea Dihydrobromide

A. 2-(2-Dimethylaminoethylamino)-5,6-dimethyl pyrazine.

2-chloro-5,6-dimethylpyrazine (12.8 g., 0.09 mole) is added to unsym-dimethylethylenediamine (26 g., 0.295 mole) containing cuprous chloride (0.25 g.) and the mixture is heated for 48 hours in an oil bath maintained at 135°-140° C. On cooling, 50 ml of water and a single molar excess of 10N sodium hydroxide are added. The mixture is extracted with methylene chloride. The organic extracts are backwashed with saturated sodium chloride solution, dried over sodium sulfate, filtered and concentrated under vacuum. The residual oil is dissolved in hexane, filtered and reconcentrated to obtain the product oil (15.8 g., 0.081 mole).

B. N,N-Dimethyl-N'-(2-dimethylaminoethyl)-N'-(5,6-dimethyl-2-pyrazinyl)urea Dihydrobromide Following the process of Example 2 using 2-(2-dimethylaminoethylamino)-5,6-dimethyl pyrazine there is obtained N,N-Dimethyl-N'-(2-dimethylaminoethyl)-N'-

(5,6-dimethyl-2-pyrazinyl)urea dihydrobromide, melting point 188° C.

EXAMPLE 4

N,N-Dimethyl-N'-(2-dimethylaminoethyl)-N'-(6-dimethyl-amino-2-pyrazinyl)urea Dihydrochloride

A. 2-Chloro-6-dimethylaminopyrazine

Cuprous chloride (50 mg) is added to a solution of dimethylamine (36 g., 0.8 mole) in 260 ml of isopropanol. 2,6-Dichloropyrazine (49.9 g., 0.33 mole) is added to the mixture with stirring and cooling to maintain the temperature at 35°–40° C. After ¾ hr. the cooling bath is removed and the reaction mixture is stored at ambient temperature for 16 hours and finally at 42°–48° C. for 3 hours. The solvent is removed under vacuum and the residue is dissolved in dilute hydrochloric acid. The aqueous solution is extracted with ether and then made basic with solid sodium bicarbonate and extracted with methylene chloride. The organic extracts are washed with brine, dried over sodium sulfate and concentrated under vacuum to obtain 49 g. of product, melting point 46°–8° C.

B. 2-(2-Dimethylaminoethylamino)-6-dimethylaminopyrazine.

Following the process of Example 3A using 2-chloro-6-dimethylaminopyrazine there is obtained, 2-(2-dimethylaminoethylamino)-6-dimethylaminopyrazine.

C. N,N-Dimethyl-N'-(2-dimethylaminoethyl)-N'-(6-dimethylamino-2-pyrazinyl)urea Dihydrochloride 2-(2-Dimethylaminoethylamino)-6-dimethylaminopyrazine (16.5 g., (0.079 mole) is dissolved in 150 ml dry toluene under nitrogen and sodium hydride (50% in mineral oil) (4.17 g., 0.087 mole) is added. The mixture is heated with stirring at 90°–98° C. for ½ hour and then refluxed for ½ hour. After cooling to 35° C. dimethylcarbamoylchloride (9.35 g., 0.087 mole) is added and the mixture is refluxed for 3 hours and cooled. Ethanol, 5 ml is added and the solvents are removed under reduced pressure. The residue is dissolved in dilute hydrochloric acid and extracted with ether. The aqueous layer is made alkaline with aqueous sodium hydroxide with a cooling bath to maintain the temperature below 35° C. The alkaline solution is extracted with methylene chloride. The organic extracts are washed with saturated sodium chloride solution, dried over sodium sulfate and concentrated under vacuum. The residual oil is dissolved in isopropanol, 50 ml and diethyl ether, 300 ml and then gaseous hydrogen chloride is passed into the solution. The product dihydrochloride crystallizes, is filtered, and washed with 100 ml of 1:1 acetone: isopropanol. Recrystallization from 150 ml isopropanol and 75 ml of diethyl ether yields 8 g. (0.029 mole) of the dihydrochloride salt, melting point 189° C. (dec).

EXAMPLE 5

N,N-Dimethyl-N'-(2-dimethylaminoethyl)-N'-(4,6-dimethyl-2-pyrimidinyl)urea Hydrochloride

A. 2-(2-Dimethylaminoethylamino)-4,6-dimethylpyrimidine

Following the procedure of Example 1-A using 2-dimethylaminoethyl chloride hydrochloride, there is obtained 2-(2-dimethylaminoethyl)-4,6-dimethylpyrimidine boiling at 90°–100° C. at 0.5 mm.

B. N,N-(Dimethyl)-N'-(2-dimethylaminoethyl)-N'-(4,6-dimethyl-2-pyrimidinyl)urea Hydrochloride Following the procedure of Example 2 using 2-(2-dimethylaminoethylamino)-4,6-dimethylpyrimidine and neutralizing with hydrogen chloride instead of hydrogen bromide, N,N-(dimethyl-N'-(2-dimethylaminoethyl)-N'-(4,6-dimethyl-2-pyrimidinyl)urea hydrochloride is obtained having a melting point of 177°–179° C.

EXAMPLE 6

N,N-Dimethyl-N'-(2-dimethylaminoethyl)-N'-(2-pyrimidinyl)urea Hydrochloride

Following the procedure of Example 2 using 2-(2-dimethylaminoethylamino) pyrimidine and neutralizing with hydrogen chloride instead of hydrogen bromide, N,N-dimethyl-N'-(2-dimethylaminoethyl)-N'-(2-pyrimidinyl)urea hydrochloride is obtained having a melting point of 182°–184° C.

EXAMPLE 7

N,N-Dimethyl-N'-(2-dimethylaminoethyl-N'-(4-methyl-6-dimethylamino-2-pyrimidinyl)urea Dihydrobromide

A. 2-Amino-4-methyl-6-dimethylaminopyrimidine

2-Amino-4-methyl-6-chloropyrimidine (52 g., 0.36 mole) is heated at 160° C. for 18 hours with ethanol and an equimolar amount of dimethylamine in a pressure vessel. The reaction mixture is evaporated in vacuo taken up in 200 ml. of water containg 50 ml. 10N sodium hydroxide and 300 ml. of methylene chloride. The mixture is extracted with methylene chloride and the organic layer dried and evaporated to dryness in vacuo affording 46 g. of 2-amino-4-methyl-6-dimethylaminopyrimidine with a melting point of 172°–174° C.

B. 2-Acetamido-4-methyl-6-dimethylaminopyrimidine

A mixture of 44 g. (0.29 moles) of 2-amino-4-methyl-6-dimethylaminopyrimidine 46 g. (0.45 moles) of acetic anhydride and 100 ml. toluene is stirred at reflux for 4 hours. The reaction mixture is cooled, 25 ml. of ethanol and 100 ml. of hexane are added and the mixture is filtered. The filtrate is evaporated in vacuo and the residue combined with 200 ml. of methylene chloride and 100 ml. of water containing excess ammonium hydroxide. The organic layer is separated and the aqueous layer extracted with methylene chloride. The combined extracts are dried with sodium sulfate and concentrated to a small volume and filtered. The filtrate is concentrated to dryness and taken up in 50 ml. of methylene chloride and filtered. The solid materials from both filtrations are combined affording 48.4 g. of 2-acetamido-4-methyl-6-dimethylamino pyrimidine melting point 153°–157° C.

C. 2-(2-Dimethylaminoethylamino)-4-methyl-6-dimethylaminopyrimidine.

Following the procedure of Example 1, Part A 2-acetamido-4-methyl-6-dimethylaminopyrimidine and 2-dimethylaminoethyl chloride hydrochloride, 2-(2-dimethylaminoethylamino)-4-methyl-6-dimethylaminopyrimidine is obtained with a boiling point of 120°–124° C. at 0.03 mm.

D.

N,N-Dimethyl-N'-(2-dimethylaminoethyl)-N'-(4-methyl-6-dimethylaminopyrimidinyl)urea Dihydrobromide Following the procedure of Example 4, Part C using 2-(2-dimethylaminoethylamino)-4-methyl-6-dimethylaminopyrimidine, and hydrogen bromide instead of hydrogen chloride for the final salt formation N,N-dimethyl-N'-(2-dimethylaminoethyl)-N'-(4-methyl-6-dimethylamino-2-pyrimidinyl)urea dihydrobromide is obtained with a melting point of 213° C.

EXAMPLE 8

N,N-Dimethyl-N'-(2-dimethylaminoethyl)-N'-(6-chloro-3-pyridazinyl)urea Hydrochloride A. 3-(2-Dimethylaminoethylamino)-6-chloropyridazine Following the procedure of Example 3, Part A using 3,6-dichloropyridazine there is obtained 3-(2-dimethylaminoethylamino)-6-chloropyridazine with melting point of 86°–92° C.

B.

N,N-Dimethyl-N'-(2-dimethylaminoethyl)-N'-(6-chloro-3-pyridazinyl)urea Hydrochloride Following the procedure of Example 2 using 3-(2-dimethylaminoethylamino)-6-chloropyridazine and forming the hydrohalide salt of the product with hydrogen chloride there is obtained N,N-dimethyl-N'-(2-dimethylaminoethyl)-N'-(6-chloro-3-pyridazinyl)urea hydrochloride with melting point of 194° C.

EXAMPLE 9

N,N-Dimethyl-N'-(2-dimethylaminoethyl)-N'-(3-pyridazinyl)urea Dihydrochloride

N,N-Dimethyl-N'-(2-dimethylaminoethyl)-N'-(6-chloro-3-pyridazinyl)urea hydrochloride (10.5 g., 0.034 mole) (Example 8) and 1.5 g. of 5% palladium on carbon catalyst are added to a mixture of 35 ml of 2N sodium hydroxide in 250 ml of ethyl alcohol. Treatment with hydrogen is performed in a Parr apparatus at 40–50 lbs. per sq. in. pressure and ambient temperature. The catalyst is removed by filtration, the filtrate is concentrated under reduced pressure, water is added and the mixture is extracted with benzene. The extracts are concentrated, the residue is dissolved in ether, hydrogen chloride is added and N,N-dimethyl-N'-(2-dimethylaminoethyl)-N'-(3-pyridazinyl)urea dihydrochloride melting at 187.5°–188.5° C. is obtained.

EXAMPLE 10

N,N-Dimethyl-N'-(2-dimethylaminoethyl)-N'-(2,6-dimethyl-4-pyrimidinyl)urea Dihydrochloride

A.

4-(2-Dimethylaminoethylamino)-2,6-dimethyl-pyrimidine

Following the procedure of Example 3, Part A using 4-chloro-2,6-dimethylpyrimidine, 4-(2-dimethylaminoethylamino)-2,6-dimethylpyrimidine is obtained as an oil which is vacuum distilled and boils at 108°–111° C. at 0.5 mm of Hg.

B.

N,N-Dimethyl-N'-(2-dimethylaminoethyl)-N'-(2,6-dimethyl-4-pyrimidinyl)urea Dihydrochloride Following the procedure of Example 2 using 4-(2-dimethylaminoethylamino)-2,6-dimethylpyrimidine and forming the hydrohalide salt of the product with hydrogen chloride there is obtained N,N-dimethyl-N'-(2-dimethylaminoethyl)-N'-(2,6-dimethyl-4-pyrimidinyl)urea dihydrochloride with melting point of 220°–222° C.

EXAMPLE 11

N,N-Dimethyl-N'-(2-dimethylaminoethyl)-N'-(3,5,6-trimethyl-2-pyrazinyl)urea Dihydrochloride

A.

2-(2-Dimethylaminoethylamino)-3,5,6-Trimethylpyrazine

Following the procedure of Example 3, Part A using 2-chloro-3,5,6-trimethylpyrazine, 2-(2-dimethylaminoethylamino)-3,5,6-trimethylpyrazine is obtained.

B.

N,N-Dimethyl-N'-(2-dimethylaminoethyl)-N'-(3,5,7-trimethyl-2-pyrazinyl)urea Dihydrochloride Following the procedure of Example 2 using 2-(2-dimethylaminoethylamino)-3,5,6-trimethylpyrazine, and forming the hydrohalide salt of the product with hydrogen chloride, N,N-dimethyl-N'-(2-dimethylaminoethyl)-N'-(3,5,6-trimethyl-2-pyrazinyl)urea dihydrochloride is obtained with a melting point of 224° C.

EXAMPLE 12

N,N-Dimethyl-N'-(2-dimethylaminoethyl)-N'-(6-methyl-2-pyrazinyl)urea Dihydrobromide A. 2-(2-Dimethylaminoethylamino)-6-methylpyrazine Following the procedure of Example 3, Part A using 2-chloro-6-methylpyrazine, 2-(2-dimethylaminoethylamino)-6-methylpyrazine is obtained as an oil.

B.

N,N-Dimethyl-N'-(2-dimethylaminoethyl)-N'-(6-methyl-2-pyrazinyl)urea Dihydrobromide Following the procedure of Example 2, using 2-(2-dimethylaminoethylamino)-6-methylpyrazine,N,N-dimethyl-N'-(2-dimethylaminoethyl)-N'-(6-methyl-2-pyrazinyl)urea dihydrobromide is obtained with a melting point of 189° C.

EXAMPLE 13

N,N-Dimethyl-N'-(2-dimethylaminoethyl)-N'-(4-pyrimidinyl)urea Dihydrochloride

A. 4-(2-Dimethylaminoethylamino)pyrimidine

A solution of 4-methoxypyrimidine (12.9 g., 0.117 mole) and unsym-dimethylethylene diamine (20.7 g., 0.23 mole) in 40 ml of xylene is heated under reflux for 64 hours. The reaction is concentrated and the oil is distilled at 15 mm of Hg. 4-(2-Dimethylaminoethylamino)pyrimidine, boiling at 164°–169° C., is collected.

B.
N,N-Dimethyl-N'-(2-dimethylaminoethyl)-N'-(4-pyrimidinyl)urea Dihydrochloride Following the procedure of Example 2, using 4-(2-dimethylaminoethylamino)pyrimidine and forming the hydrohalide salt of the product with hydrogen chloride, there is obtained N,N-dimethyl-N'-(2-dimethylaminoethyl)-N'-(4-pyrimidinyl)urea dihydrochloride with a melting point of 206°–208° C.

EXAMPLE 14
N,N-Dimethyl-N'-(2-diisopropylaminoethyl)-N'-(2-pyrazinyl)urea Dihydrobromide A. 2-(2-Diisopropylaminoethylamino)pyrazine Following the procedure of Example 3, Part A using 2-chloropyrazine and unsym-diisopropylethylenediamine, 2-(2-diisopropylaminoethylamino)pyrazine is obtained with a boiling range of 180°–190° C. upon distillation at 17 mm. of Hg.

B.
N,N-Dimethyl-N'-(2-diisopropylaminoethyl)-N'-(2-pyrazinyl)urea Dihydrobromide Following the procedure of Example 4, Part C using 2-(2-diisopropylaminoethylamino)pyrazine and forming the hydrohalide salt with hydrogen bromide, N,N-dimethyl-N'-(2-diisopropylaminoethyl)-N'-(2-pyrazinyl)urea dihydrobromide with melting point of 186°–188° C. is obtained.

EXAMPLE 15
N,N-Dimethyl-N'-(2-dimethylaminoethyl)-N'-(6-chloro-2-pyrazinyl)urea Hydrobromide A. 2-(2-Diethylaminoethylamino)-6-Chloropyrazine Following the procedure of Example 3, Part A using 2,6-dichloropyrazine, 2-(2-dimethylaminoethylamino)-6-chloropyrazine is obtained as an oil.

B.
N,N-Dimethyl-N'-(2-dimethylaminoethyl)-N'-(6-chloro-2-pyrazinyl)urea Hydrobromide Following the procedure of Example 2, using 2-(2-dimethylaminoethylamino)-6-chloropyrazine, N,N-dimethyl-N'-(2-dimethylaminoethyl)-N'-(6-chloro-2-pyrazinyl)urea hydrobromide with a melting point of 159.5°–161° C. is obtained.

EXAMPLE 16
N,N-Dimethyl-N'-(2-dimethylaminoethyl)-N'-(3,6-dimethyl-2-pyrazinyl)urea A. 2-(2-Dimethylaminoethylamino)-3,6-dimethylpyrazine Following the procedure of Example 3, Part A using 2-chloro-3,6-methylpyrazine, 2-(2-dimethylaminoethylamino)-3,6-dimethylpyrazine is obtained as an oil which is distilled at 0.5 mm of Hg. and collected at a boiling point of 89.5°–91.5° C.

B.
N,N-Dimethyl-N'-(2-dimethylaminoethyl)-N'-(3,6-dimethyl-2-pyrazinyl)urea

Following the procedure of Example 2 using 2-(2-dimethylaminoethylamino)-3,6-dimethylpyrazine and omitting hydrohalide salt formation, N,N-dimethyl-N'-(2-dimethylaminoethyl)-N'-(3,6-dimethyl-2-pyrazinyl)urea is obtained with melting point of 96°–98° C.

EXAMPLE 17
N,N-Dimethyl-N'-(2-dimethylaminoethyl)-N'-[3-(1,2,4-triazinyl)]urea Hydrochloride A. 3-(2-Dimethylaminoethylamino)-1,2,4-triazine 3-Methylthio-1,2,4-triazine (19.1 g., 0.15 mole) and unsym-dimethylethylene diamine (35.2 g., 0.40 mole) are dissolved in 100 ml of isopropyl alcohol and the mixture is heated under reflux in a nitrogen atmosphere for five days. The solvent is removed under reduced pressure and the residue is distilled at 0.5 mm of Hg. 3-(2-Dimethylaminoethylamino)-1,2,4-triazine is collected at 168°–169° C.

B.
N,N-Dimethyl-N'-(2-dimethylaminoethyl)-N'-[3-(1,2,4-triazinyl)]urea Hydrochloride Following the procedure of Example 2, using 3-(2-dimethylaminoethylamino)-1,2,4-triazine and forming the hydrohalide salt of the product with hydrogen chloride, there is obtained N,N-dimethyl-N'-(2-dimethylaminoethyl)-N'-[3-(1,2,4-triazinyl)] urea hydrochloride with melting point of 192°–193° C.

EXAMPLE 18
N,N-Dimethyl-N'-(2-diisopropylaminoethyl)-N'-(4-methyl-6-benzyloxy-2-pyrimidinyl)urea A. 2-Amino-4-methyl-6-benzyloxypyrimidine 2-Amino-4-methyl-6-hydroxypyrimidine (62.5 g., 0.50 mole) is dissolved in 500 ml of dimethylformamide and sodium hydride (0.5 mole) is added over a 1 hour period under a nitrogen atmosphere. The mixture is heated at 75° C. for 1½ hours. Benzyl chloride (69.3 g., 0.55 moles) is then added over 15 minutes and the mixture is heated at 90° C. and stirred for 1½ hours. After cooling, the reaction mixture is filtered and concentrated under vacuum to an oil from which 2-amino-4-methyl-6-benzyloxypyrimidine melting at 108°–109.5° C. is obtained by crystallization from n-butyl chloride.

B. 2-Acetamido-4-methyl-6-benzyloxypyrimidine

Acetic anhydride (15.3 g., 0.15 mole) is added to a stirred suspension of 2-amino-4-methyl-6-benzyloxypyrimidine (23.6 g., 0.11 mole) in 150 ml of benzene. The mixture is heated at reflux for 4 hours. It is cooled, neutralized with aqueous sodium carbonate and the benzene layer separated. The benzene solution is concentrated under vacuum to an oil from which 2-acetamido-4-methyl-6-benzyloxy-pyrimidine melting at 121°–122° C. is isolated by crystallization from hexane n-butyl chloride.

C.
2-(2-Diisopropylaminoethylamino)-4-methyl-6-hydroxy-pyrimidine

Following the procedure of Example 1 part A using 2-acetamido-4-methyl-6-benzyloxypyrimidine and conducting the final hydrolysis with 3N hydrochloric acid, there is obtained 2-(2-diisopropylaminoethylamino)-4-methyl-6-hydroxypyrimidine.

D.
2-(2-Diisopropylaminoethylamino)-4-methyl-6-benzyloxy-pyrimidine

Following the procedure of part A using 2-(2-diisopropylaminoethylamino)-4-methyl-6-hydroxypyrimidine, 2-(2-diisopropylaminoethylamino)-4-methyl-6-benzyloxypyrimidine is obtained as an oil which is distilled at 0.6 mm of Hg and is collected at 198°–200° C.

E.
N,N-Dimethyl-N'-(2-diisopropylaminoethyl)-N'-(4-methyl-6-benzyloxy-2-pyrimidinyl)urea Under a nitrogen atmosphere, n-butyl lithium solution (22.2 ml, 0.036 mole) is added dropwise with stirring to a solution of 2-(2-diisopropylaminoethylamino)-4-methyl-6-benzyloxypyrimidine (12.4 g., 0.036 mole) in 75 ml. of dry benzene at 25° to 30° C. with occasional cooling over a 20 minute period. After stirring an additional ¾ hour, dimethylcarbamoyl chloride (4.3 g., 0.04 mole) is added dropwise over 15 minutes. The reaction is stirred at room temperature for 16 hours. After cooling, the reaction mixture is treated with water and the benzene layer is separated. The crude product is extracted into 1N-hydrochloric acid. This aqueous solution is basified and the product is extracted into ether, dried over sodium sulfate, filtered and concentrated in vacuo. Chromatography on silica gel eluting with 25% methanol, 75% chloroform yields N,N-dimethyl-N'-(2-diisopropylaminoethyl)-N -(4-methyl-6-benzyloxy-2-pyrimidinyl)urea.

EXAMPLE 19
N,N-Dimethyl-N'-(2-diisopropylaminoethyl)-N'-(4-methyl-6-hydroxy-2-pyrimidinyl)urea Hydrochloride N,N-Dimethyl-N'-(2-diisopropylaminoethyl)-N'-(4-methyl-6-benzyloxy-2-pyrimidinyl) urea (3.4 g., 0.0082 mole) is dissolved in 50 ml of ethyl alcohol and 0.3 g. of 10% palladium on carbon catalyst is added. Hydrogenolytic debenzylation is conducted at 30 lbs. per sq. in., the catalyst is removed, hydrogen chloride is added and N,N-dimethyl-N'-(2-diisopropylaminoethyl)-N'-(4-methyl-6-hydroxy-2-pyrimidinyl)urea hydrochloride melting (dec.) at 198°–208° C. is obtained.

EXAMPLE 20
N,N-Dimethyl-N'-(2-dimethylaminoethyl)-N'-(5-chloro-2-pyrimidinyl)urea Dihydrobromide

A. 2-(2-Dimethylaminoethylamino)-5-chloropyrimidine

Following the procedure of Example 1 part A and replacing the 2-acetamido-4,6-dimethylpyrimidine and 2-diisopropylaminoethyl chloride hydrochloride with equivalent amounts of 2-acetamido-5-chloropyrimidine and 2-dimethylaminoethyl chloride hydrochloride respectively, there is obtained 2-(2-dimethyl-aminoethylamino)-5-chloropyrimidine which is distilled at 115°–118° C. at 1.8 mm of mercury.

B.
N,N-Dimethyl-N'-(2-dimethylaminoethyl)-N'-(5-chloro-2-pyrimidinyl)urea Dihydrobromide Following the procedure of Example 18 part E using 2-(2-dimethylaminoethylamino)-5-chloropyrimidine and forming the hydrohalide salt of the product with hydrogen bromide, N,N-dimethyl-N'-(2-dimethylaminoethyl)-N'-(5-chloro-2-pyrimidinyl)urea dihydrobromide melting at 182° C. is obtained.

EXAMPLE 21
N,N-Dimethyl-N'-(2-diisopropylaminoethyl)-N'-(4,6-dimethyl-5-chloro-2-pyrimidinyl)urea Hydrochloride

A. N,N-Dimethyl-N'-(4,6-dimethyl-5-chloro-2-pyrimidinyl)urea

Sodium hydride (6 g., 55%, 0.137 mole) is added to a mixture of 2-amino-4,6-dimethyl-5-chloropyrimidine (19.5 g., 0.125 mole) in 250 ml of toluene. The mixture, under a nitrogen atmosphere is heated to reflux and stirred for one hour. Another portion of sodium hydride (6 g., 55%, 0.137 mole) is added and after two hours of reflux, dimethyl carbamoyl chloride (13.9 g., 0.125 mole) is added. After one hours of reflux the reaction is cooled, water is added, the toluene is removed by vacuum concentration and the product is extracted into petroleum ether from which it is crystallized by evaporation. N,N-Dimethyl-N'-(4,6-dimethyl-5-chloro-2-pyrimidinyl)urea melting at 127°–129° C. is obtained.

B.
N,N-Dimethyl-N'-(2-diisopropylaminoethyl)-N'-(4,6-dimethyl-5-chloro-2-pyrimidinyl)urea Hydrochloride The product of part A (12.8 g., 0.056 mole) is dissolved in 185 ml of dioxane, lithium hydride (1.16 g., 0.146 mole) is added and the mixture is stirred under nitrogen at reflux. Diisopropylaminoethyl chloride hydrochloride (11.2 g., 0.056 mole) is added and the mixture is heated under reflux for eight hours. Water (20 ml) and isopropyl alcohol (20 ml) are added and the mixture is concentrated in vacuo. Water (100 ml) and saturated sodium carbonate are added and the mixture is extracted with methylene. The combined extract is concentrated, ethanolic hydrogen chloride is added and N,N-dimethyl-N'-(2-diisopropylaminoethyl)-N-(4,6-dimethyl-5-chloro-2-pyrimidinyl)urea hydrochloride is crystallized from ether. The melting point is 202°–204° C.

EXAMPLE 22
N-(2-Diisopropylaminoethyl)-N-(4,6-dimethyl-2-pyrimidinyl)urea

A. Phenyl N-(2-diisopropylaminoethyl)-N-(4,6-dimethyl-2-pyrimidinyl)carbamate Hydrochloride A solution of 2-(2-diisopropylaminoethylamino)-4,6-dimethylpyrimidine (12.5 g., 0.05 mole) in 50 ml of benzene is added to a solution of phenyl chloroformate in 50 ml of benzene. After 72 hours, the solid product is collected and recrystallized from acetone to give phenyl N-(2-diisopropylaminoethyl)-N-(4,6-dimethyl-2-pyrimidinyl)carbamate hydrochloride melting at 190°–202° C.

B.
N-(2-Diisopropylaminoethyl)-N-(4,6-dimethyl-2-pyrimidinyl)urea

Concentrated ammonia (10 ml) is added to a solution of phenyl N-(2-diisopropylaminoethyl)-N-(4,6-dimethyl-2-pyrimidinyl)carbamate hydrochloride (7.33 g., 0.018 mole) in 50 ml of tetrahydrofuran and the mixture is allowed to stand for twenty-four hours. It is concentrated, water and chloroform are added to the residue, the chloroform is separated and concentrated. Crystallization of the residue from hexane yields N-(2-diisopropylaminoethyl)-N-(4,6-dimethyl-2-pyrimidinyl)urea melting at 134°–136° C.

EXAMPLE 23

N-(2-Dimethylaminoethyl)-N-(2-pyrazinyl)urea

A.

N-(2-Dimethylaminoethyl)-N-(2-pyrazinyl)cyanamide

A solution of cyanogen bromide (15.9 g., 0.150 mole) in 75 ml of tetrahydrofuran is added to a solution of 2-(2-dimethylaminoethylamino)pyrazine (16.6 g., 0.1 mole) and triethylamine (20.9 g., 0.15 mole) in 100 ml of tetrahydrofuran. After 72 hours, dilute sodium hydroxide is added and the mixture is extracted with ether. The extracts are concentrated and the residue is distilled under reduced pressure. N-(2-Dimethylaminoethyl)-N-(2-pyrazinyl)cyanamide boiling at 130°–132° C. at 0.7 mm is collected.

B. N-(2-Dimethylaminoethyl)-N-(2-pyrazinyl)urea

N-(2-Dimethylaminoethyl)-N-(2-pyrazinyl)cyanamide (2.83 g., 0.015 mole) is dissolved in 20 ml of 6N hydrochloric acid. After one hour, the mixture is made alkaline with concentrated sodium hydroxide and concentrated. The residue is extracted with ether which is concentrated. The residue is crystallized from butyl chloride and N-(2-dimethylaminoethyl)-N-(2-pyrazinyl)urea melting at 105°–108° C. is obtained.

EXAMPLE 24

N,N-Dimethyl-N'-(2-dimethylaminoethyl)-N'-[5,6-dimethyl-3-(1,2,4-triazinyl)]urea Hydrochloride

A.

3-(2-Dimethylaminoethylamino)-5,6-dimethyl-1,2,4-triazine

Following the procedure of Example 17 part A using 3-methylthio-5,6-dimethyl-1,2,4-triazine, 3-(2-dimethylaminoethylamino)-5,6-dimethyl-1,2,4-triazine is obtained with a melting point of 46°–49° C.

B.

N,N-Dimethyl-N'-(2-dimethylaminoethyl)-N'-[5,6-dimethyl-3-(1,2,4-triazinyl)]urea Hydrochloride Following the procedure of Example 2 using 3-(2-dimethylaminoethylamino) 5,6-dimethyl-1,2,4-triazine and forming the hydrohalide salt of the product with hydrogen chloride, there is obtained N,N-dimethyl-N'-(2-dimethylaminoethyl)-N'-[5,6-dimethyl-3-(1,2,4-triazinyl)]urea hydrochloride melting at 173°–175° C.

EXAMPLE 25

N-(2-Dimethylaminoethyl)-N-(4,6-dimethyl-2-pyrimidinyl)-N'-ethylurea Hydrochloride A solution of 11.6 g., (0.06 mole) of 2-(2-dimethylaminoethylamino)-4,6-dimethylpyrimidine in 150 ml. of benzene is dried by azeotropic distillation. The solution is then treated with 8.5 g. (0.120 mole) of ethyl isocyanate and heated at reflux for 24 hours. After removal of the solvent, the residue is dissolved in 100 ml of ethyl ether and the solution is neutralized with 3 ml of 10.6 N hydrogen chloride in ethanol. The resulting white precipitate is recrystallized from isopropanol to give N-(2-dimethylaminoethyl)-N-(4,6-dimethyl-2-pyrimidinyl)-N'-ethylurea hydrochloride.

EXAMPLE 26

N,N-Dimethyl-N'-(2-dimethylaminoethyl)-N'-(3,6-dimethyl-2-pyrazinyl)thiourea

A solution of 11.6 g. (0.06 mole) of 2-dimethylaminoethylamino-3,6-dimethylpyrazine in 175 ml of dry tetrahydrofuran is allowed to react with 40.8 ml (0.066 mole) of 1.62 M butyl lithium in hexane. Then 8.16 g. (0.066 mole) of dimethyl thiocarbamoyl chloride in 75 ml of dry tetrahydrofuran is added over 20 minutes with ice cooling. The reaction mixture is allowed to stir overnight at room temperature. After quenching with water, the product is extracted into ether. The ether extract is washed with water and saturated sodium chloride solutions and dried over magnesium sulfate. The crude product is obtained as a brown oil.

The crude product is chromatographed on silica gel, eluting with 5% methanol in chloroform. After combining the appropriate fractions, the solvent is removed in vacuum and the residue distilled through a short path still. There is obtained N,N-dimethyl-N'-(2-dimethylaminoethyl)-N'-(3,6-dimethyl-2-pyrazinyl)thiourea.

EXAMPLE 27

N-(2-Dimethylaminoethyl)-N-(2-pyrazinyl)-N'-methylthiourea Hydrochloride

Following the procedure of Example 25 using 2-(2-dimethylaminoethylamino)pyrazine and methylisothiocyanate, there is obtained N-(2-dimethylaminoethyl)-N-(2-pyrazinyl)-N'-methylthiourea hydrochloride.

EXAMPLE 28

N,N-Dimethyl-N'-(2-methyl-3-dimethylaminopropyl)-N'-(5-chloro-2-pyrimidinyl)urea

A.

2-(2-Methyl-3-dimethylaminopropylamino)-5-chloropyrimidine

Following the procedure of Example 1 part A using 2-acetamido-5-chloropyrimidine and 2-methyl-3-dimethylaminopropyl chloride hydrochloride, there is obtained 2-(2-methyl-3-dimethylamino-propylamino)-5-chloropyrimidine.

B.

N,N-Dimethyl-N'-(2-methyl-3-dimethylaminopropyl)-N'-(5-chloro-2-pyrimidinyl)urea Following the procedure of Example 1 part B using 2-(2-methyl-3-dimethylaminopropylamino)-5-chloropyrimidine there is obtained N,N-dimethyl-N'-(2-methyl-3-dimethylaminopropyl)-N'-(5-chloro-2-pyrimidinyl)urea.

EXAMPLE 29

N,N-Dimethyl-N'-(2-methyl-2-dimethylaminopropyl)-N'-(4-methyl-6-dimethylamino-2-pyrimidinyl)urea

A.

2-(2-Methyl-2-dimethylaminopropylamino)-4-methyl-6-dimethylaminopyrimidine

Following the procedure of Example 1 part A using 2-acetamido-4-methyl-6-dimethylaminopyrimidine and 2-methyl-2-dimethylaminopropyl chloride hydrochloride, there is obtained 2-(2-methyl-2-dimethylaminopropylamino)-4-methyl-6-dimethylaminopyrimidine.

B.
N,N-Dimethyl-N'-(2-methyl-2-dimethylaminopropyl)-N'-(4-methyl-6-dimethylamino-2-pyrimidinyl)urea Following the procedure of Example 1 part B using 2-(2-methyl-2-dimethylaminopropylamino)-4-methyl-6-dimethylaminopyrimidine, there is obtained N,N-dimethyl-N'-(2-methyl-2-dimethylaminopropyl)-N'-(4-methyl-6-dimethylamino-2-pyrimidinyl)urea.

EXAMPLE 30

N,N-Diethyl-N'-(2-diisopropylaminoethyl)-N'-(2-pyrazinyl)urea Hydrochloride

Following the procedure of Example 4 part C using 2-(2-diisopropylaminoethylamino)pyrazine and diethylcarbamoylchloride, there is obtained N,N-diethyl-N'-(2-diisopropylaminoethyl)-N'-(2-pyrazinyl)urea hydrochloride.

What is claimed is:

1. A compound having the formula:

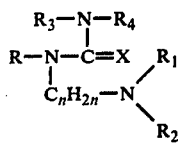

wherein R is pyrimidinyl which may be optionally substituted with from 1 to 3 of loweralkyl, halo, hydroxy, amino, mono or di-loweralkylamino, loweralkoxy or phenylloweralkoxy;

$R_1$ and $R_2$ are independently loweralkyl;

$R_3$ and $R_4$ are independently hydrogen or loweralkyl;

X is oxygen or sulfur; and n is an integer of from 2 to 6, such that the direct linkage between the nitrogen atoms is either two or three carbon atoms, and the pharmaceutically acceptable acid addition salts thereof.

2. The compound of claim 1 wherein R is pyrimidinyl, optionally substituted with 1 to 3 of methyl, chloro or dimethylamino;

$R_1$, $R_2$, $R_3$ and $R_4$ are independently methyl, ethyl or isopropyl;

n is 2; and

X is oxygen.

3. The compound of claim 2 wherein R is pyrimidinyl substituted with 1 or 2 methyl groups or a chloro and 2 methyl groups;

$R_1$ and $R_2$ are isopropyl; and $R_3$ and $R_4$ are methyl.

4. The compound of claim 1 which is N,N-dimethyl-N'-(2-dimethylaminoethyl)-N'-(2-pyrimidinyl)urea.

5. The compound of claim 1 which is N,N-dimethyl-N'-(2-dimethylaminoethyl) N'(4,6-dimethyl-2-pyrimidinyl)urea.

6. The compound of claim 1 which is N,N-dimethyl-N'-(2-diisopropylaminoethyl)-N'-(4,6-dimethyl-2-pyrimidinyl)urea.

7. The compound of claim 1 which is N,N-dimethyl-N'-(2-diisopropylaminoethyl)-N'-(4,6-dimethyl-5-chloro-2-pyrimidinyl)urea.

8. The compound of claim 1 which is N-(2-diisopropylaminoethyl)-N-(4,6-dimethyl-2-pyrimidinyl)urea.

9. A composition for the inhibition of gastric acid secretion which comprises an inert carrier and a compound having the formula:

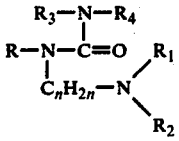

wherein R is pyrimidinyl which may be optionally substituted with from 1 to 3 of loweralkyl, halo, hydroxy, amino, mono or di-loweralkylamino, loweralkoxy, or phenyl loweralkoxy: and $R_1$ and $R_2$, are independently loweralkyl;

$R_3$ and $R_4$ are independently hydrogen or loweralkyl; and n is an integer of from 2 to 6, such that the direct linkage between the nitrogen atoms is either two or three carbon atoms, and the pharmaceutically acceptable acid addition salt thereof.

* * * * *